(12) United States Patent
Zhao

(10) Patent No.: US 6,451,358 B2
(45) Date of Patent: Sep. 17, 2002

(54) COMPOSITION AND METHOD FOR THE TREATMENT OF VITILIGO

(75) Inventor: Huiping Zhao, Etobicoke (CA)

(73) Assignee: Mileuna, Inc., Ontario (CA)

( * ) Notice: Subject to any disclaimer, the term of this patent is extended or adjusted under 35 U.S.C. 154(b) by 0 days.

(21) Appl. No.: 09/750,897

(22) Filed: Dec. 28, 2000

Related U.S. Application Data

(60) Provisional application No. 60/173,527, filed on Dec. 29, 1999.

(51) Int. Cl.7 .......................... A01N 65/00; A61K 35/78
(52) U.S. Cl. .......................... 424/746; 424/725; 424/773
(58) Field of Search ................................ 424/725, 773, 424/746

(56) References Cited

U.S. PATENT DOCUMENTS

| | | | | |
|---|---|---|---|---|
| 5,411,733 A | * | 5/1995 | Hozumi et al. | 514/520 |
| 5,958,437 A | * | 9/1999 | Zaveri | 424/401 |
| 5,962,044 A | * | 10/1999 | Harris | 426/2 |
| 6,068,845 A | * | 5/2000 | Aoki et al. | 424/725 |

OTHER PUBLICATIONS

Computer WPIDS Abstract 2001–408965 Bernardo BR 9907396 "Natural herbs based treatment of vitiligo" Jun. 26, 2001.*

Computer WPIDS Abstract 2000–476405 Cheng et al CN1192368 "External use pharmaceutical compositions for treating vitiligo and its prepn methods" Sep. 19, 1998.*

* cited by examiner

Primary Examiner—Herbert J. Lilling
(74) Attorney, Agent, or Firm—Gifford, Krass, Groh, Sprinkle, Anderson & Citkowski, P.C.

(57) ABSTRACT

Compositions and methods for the treatment of vitiligo. The composition comprises at least one member selected from the group consisting of: *Eclipta prostrata* L., *Angelica dahurica* (Fish. ex. Hoffm), *Polygonum multiforum* Thumb, *Astragalus complanatus, Tribulus terrestris* L., *Lithospermum erythrorhizon* sieb et zucc, *Paris petiolata* (Bak. ex Forb), *Salvia multiorrhiza* Bge, *Sophora flavescens* Ait, *Atractylodes lancea* (Thumb) Dc, and combinations thereof. The method comprises treating the vitiligo by orally administering this composition to the patient. The treatment may be further enhanced by topically administering to the affected areas a composition selected from the group consisting of: a preparation of sulfur and kerosene; a preparation of *Nevlum oporum* solund and alcohol; a preparation of *Cinnamomum cassia* presl, *Psoralea corylifalia* L., alcohol and water; and a preparation of *Portulaca oleracea* L., brown sugar, and vinegar.

12 Claims, No Drawings

COMPOSITION AND METHOD FOR THE TREATMENT OF VITILIGO

REFERENCE TO RELATED APPLICATION

This application claims priority from Provisional Patent Application No. 60/173,527, filed Dec. 29, 1999.

FIELD OF THE INVENTION

This invention relates generally to treatment of skin conditions and, more specifically, to the treatment of vitiligo. Most specifically, the invention relates to compositions for the treatment of vitiligo, and methods for their use.

BACKGROUND OF THE INVENTION

Vitiligo, also referred to as leucoderma, is a skin condition characterized by patchy loss of pigmentation from a person's skin. The specific causes of vitiligo are unknown; however, the depigmented areas are lacking in the skin pigment melanin, and it is believed that the disease is the result of the destruction or inhibition of the melanin secreting melanocytes in the affected areas. There may be some hereditary component to the disease, since approximately 30% of the cases have a familial correlation. It is speculated that the disease may be the result of an autoimmune condition. It is also possible that a specific metabolic defect may be involved, and in some instances, environmental factors appear to play a role.

In some instances, vitiligo can be treated with topical corticosteroids, which can stimulate melanin production, possibly by reducing immune reactions. In some instances, melanin production is stimulated by treating the patient with photosensitizing drugs such as psoralen, and then exposing the affected areas of the patient to ultraviolet light. In those instances where the depigmentation is not too extreme, cosmetic preparations may be used as a cover up. Some limited use of skin grafts has also been made. In many instances, treatment is unsuccessful, and some patients opt for chemical bleaching of the remaining pigmented skin so as to produce an even complexion. As will be appreciated, the foregoing treatments are often very harsh and frequently ineffective. Therefore, there is still a need for improved treatment methodologies.

SUMMARY OF THE INVENTION

The present invention is directed to materials and methods for the treatment of vitiligo. In its broadest aspect, the composition comprises at least one member selected from the group consisting of: *Eclipta prostrata* L., *Angelica dahurica* (Fish. ex. Hoffm), *Polygonum multiforum* Thumb, *Astragalus complanatus*, *Tribulus terrestris* L., *Lithospermum erythrorhizon* sieb et zucc, *Paris petiolata* (Bak. ex Forb), *Salvia multiorrhiza* Bge, *Sophora flavescens* Ait, *Atractylodes lancea* ; (Thumb) Dc, and combinations thereof. In particular, the *Eclipta prostrata* L. may be present in the composition in a range of between 10–20 weight percent. The *Angelica dahurica* may be present in the composition in a range of between 10–20 weight percent. The *Polygonum multiforum* Thumb is present in the composition in a range of between 8–15 weight percent. The *Astragalus complanatus* may be present in the composition in a range of between 8–15 weight percent. The *Tribulus terrestris* L. may be present in the composition in a range of between 8–15 weight percent. The *Lithospermum erythrorhizon* sieb et zucc may be present in the composition in a range of between 5–10 weight percent. The *Paris petiolata* may be present in the composition in a range of between 5–10 weight percent. The *Salvia multiorrhiza* Bge may be present in the composition in a range of between 5–10 weight percent. The *Sophora flavescens*; Ait may be present in the composition in a range of between 5–10 weight percent. The *Atractylodes lancea* may be present in the composition in a range of between 0–6 weight percent.

Further aspects of the compositions of the present invention include enhancing the efficacy thereof by the application of one or more topical agents. A first embodiment of a topical agent is sulfur and kerosene. A second embodiment comprises ground *Nevlum oporum* solund in alcohol, and preferably ethyl alcohol. A third embodiment comprises *Cinnamomum cassia* presl, chopped *Psoralea corylifalia* L., alcohol (preferably ethyl alcohol) and water. A fourth embodiment comprises *Portulaca oleracea* L., brown sugar and vinegar. Typically, these topical treatment compositions are prepared by mixing the solid and liquid ingredients, allowing the mixture to stand for an extended period of time, and separating the supernatant liquid from the solids.

A particularly preferred embodiment of the composition of the present invention comprises, by weight:

| | |
|---|---|
| *Eclipta prostrata* L. | 100 g |
| *Angelica dahurica* (Fish. ex. Hoffm) | 100 g |
| *Polygonum multiforum* Thumb | 80 g |
| *Astragalus complanatus* | 80 g |
| *Tribulus terrestris* L. | 80 g |
| *Lithospermum erythrorhizon* sieb et zucc | 55 g |
| *Paris petiolata* (Bak. ex Forb) | 50 g |
| *Salvia multiorrhiza* Bge | 50 g |
| *Sophora flavescens* Ait | 50 g |
| *Atractylodes lancea* (Thumb) Dc | 25 g. |

The method of the present invention comprises administering to the patient a composition comprising: *Eclipta prostrata* L., *Angelica dahurica* (Fish. ex. Hoffm), *Polygonum multiforum* Thumb, *Astragalus complanatus*, *Tribulus terrestris* L., *Lithospermum erythrorhizon* sieb et zucc, *Paris petiolata* (Bak. ex Forb), *Salvia multiorrhiza* Bge, *Sophora flavescens* Ait, *Atractylodes lancea* (Thumb) Dc, and combinations thereof. Preferably, the composition is administered orally, and the treatment may be further enhanced by topically administering a composition selected from the group consisting of: a preparation of sulfur and kerosene; a preparation of *Nevlum oporum* solund and alcohol; a preparation of *Cinnamomum cassia* presl, *Psoralea corylifalia* L., alcohol and water; and a preparation of *Portulaca oleracea* L., brown sugar, and vinegar.

DETAILED DESCRIPTION OF THE INVENTION

The present invention is directed to materials and methods for the treatment of vitiligo. Treatment methodology includes ingestion of a systemic preparation, most preferably coupled with the application of topical treatment agents. The systemic composition is based upon combinations of herbal materials and a particularly preferred combination comprises:

| | |
|---|---|
| *Eclipta prostrata* L. | 100 g |
| *Angelica dahurica* (Fish. ex. Hoffm) | 100 g |
| *Polygonum multiforum* Thumb | 80 g |

-continued

| | |
|---|---|
| Astragalus complanatus | 80 g |
| Tribulus terrestris L. | 80 g |
| Lithospermum erythrorhizon sieb et zucc | 55 g |
| Paris petiolata (Bak. ex Forb) | 50 g |
| Salvia multiorrhiza Bge | 50 g |
| Sophora flavescens Ait | 50 g |
| Atractylodes lancea (Thumb) Dc | 25 g |

The foregoing materials are pulverized and filled into capsules, or pressed into tablets. A typical daily dosage of the material is 6 grams, preferably taken in three two-gram portions. While the foregoing composition represents one preferred embodiment, it will be appreciated by those of skill in the art that proportions of the various ingredients may be increased or decreased in accord with the present invention. In many instances, compositions including fewer than all of the above listed ingredients will be effective. Also, one of skill in the art will readily appreciate that other species of the listed materials may, in some instances, be substituted, as may be materials having equivalent effect.

While the systemic composition has been found to be effective in the treatment of vitiligo, the efficacy thereof is further increased if therapy is combined with the application of one or more topical agents. A first topical agent useful in practicing the present invention is prepared by mixing 10 g of sulphur powder with 100 ml of kerosene. The mixture is allowed to stand for seven days after which supernatant liquid is drained away from the powder. This liquid is the active composition which is applied to the affected areas.

A second topical composition may be prepared by mixing 20 g of ground *Nevlum oporum* solund with 100 ml of alcohol, which is most preferably ethyl alcohol. This mixture is allowed to stand for seven days, and the supernatent liquid, which comprises the topical agent, is separated. This agent is then applied to the affected areas.

A third topical composition is prepared by mixing 30 g of chopped *Cinnamomum cassia* presl, 90 g of chopped *Psoralea corylifalia* L. with 50 ml of alcohol (preferably ethyl alcohol) and 50 ml of water. This mixture is allowed to stand for seven days, and the supernatent is separated and used as the topical agent. Again, this agent is applied as required to the affected areas.

Finally, a fourth topical composition may be prepared by mixing 20 g of chopped *Portulaca oleracea* L., 10 g of brown sugar and 70 ml of vinegar (approximately 5% aqueous solution of acetic acid). This mixture is allowed to stand for seven days, and the supernatent liquid, which comprises the therapeutic agent, is separated from the solids and applied to the skin as required.

Of the foregoing topical compositions, the first three are considered to be fairly strong agents, while the fourth is relatively mild. Any one or more of the foregoing topical agents are used in combination with the systemic therapy, and are most preferably applied to the skin three times a day.

The treatment agents of the present invention have been found to be highly effective in bringing out repigmentation of areas of the skin manifesting vitiligo. Both the systemic and topical compositions are low in toxicity, and can be administered for relatively long periods of time; although, marked improvement of the condition is generally noted following thirty days of treatment. As discussed above, various modifications and substitutions to the compositions of the present invention will be readily apparent to one of skill in the art. Therefore, it is to be understood that the foregoing examples are meant to illustrate particular embodiments of the invention, but are not meant to be limitations upon the practice thereof. It is the following claims, including all equivalents, which define the scope of the invention.

What is claimed is:

1. A composition for the treatment of vitilifo comprising: *Eclipta prostrata* L., *Angelica dahurica*, *Polygonum multiforum* Thumb, *Astragaulus complanatus*, *Tribulus terrestris* L., *Lithospermum erythrorhizon* sieb et zucc, *Paris petiolata*, *Salvia multiorrhiza* Bge, *Sophora flavescens* Ait and *Atractylodes lancea* Dc.

2. The composition of claim 1 wherein the *Eclipta prostrata* L. is present in the composition in a range of between 10–20 weight percent.

3. The composition of claim 1 wherein the *Angelica dahurica* is present in the composition in a range of between 10–20 weight percent.

4. The composition of claim 1 wherein the *Polygonum muliforum* Thumb is present in the composition in a range of between 8–15 weight percent.

5. The composition of claim 1 wherein the *Astragalus complanatus* is present in the composition in a range of between 8–15 weight percent.

6. The composition of claim 1 wherein the *Tribulus terrestris* L. is present in the composition in a range of between 8–15 weight percent.

7. The composition of claim 1 wherein the *Lithospermum erythrorhizon* sieb et zucc is present in the composition in a range of between 5–10 weight percent.

8. The composition of claim 1 wherein the *Paris petiolata* is present in the composition in a range of between 5–10 weight percent.

9. The composition of claim 1 wherein the *Salvia multiorrhiza* Bge is present in the composition in a range of between 5–10 weight percent.

10. The composition of claim 1 wherein the *Sophora flavescens* Ait is present in the composition in a range of between 5–10 weight percent.

11. The composition of claim 1 wherein the *Atractylodes lancea* Dc is present in the composition in a range of between 0–6 weight percent.

12. A composition for the treatment of vitiligo comprising, by weight:

| | |
|---|---|
| Eclipta prostrata L. | 100 g |
| Angelica dahurica (Fish. ex. Hoffm) | 100 g |
| Polygonum multiforum Thumb | 80 g |
| Astragalus complanatus | 80 g |
| Tribulus terrestris L. | 80 g |
| Lithospermum erythrorhizon sieb et zucc | 55 g |
| Paris petiolata (Bak. ex Forb) | 50 g |
| Salvia multiorrhiza Bge | 50 g |
| Sophora flavescens Ait | 50 g |
| Atractylodes lancea (Thumb) Dc | 25 g. |

* * * * *